United States Patent [19]

Daneshy

[11] 3,987,669
[45] Oct. 26, 1976

[54] METHOD OF DETERMINING THE RELATIVE FRACTURABILITY OF MATERIALS

[75] Inventor: Abbas Ali Daneshy, Duncan, Okla.

[73] Assignee: Halliburton Company, Duncan, Okla.

[22] Filed: Mar. 1, 1976

[21] Appl. No.: 662,625

[52] U.S. Cl. .............................. 73/88 R; 73/88 E; 73/94
[51] Int. Cl.² .......................................... G01N 3/08
[58] Field of Search ............ 73/88 R, 88 E, 87, 151, 73/94, 89

[56] References Cited
UNITED STATES PATENTS

| 642,979 | 2/1900 | Haase | 73/94 |
| 2,671,344 | 3/1954 | Raven | 73/94 |
| 3,580,334 | 5/1971 | Broussard et al. | 73/94 |

*Primary Examiner*—James J. Gill
*Assistant Examiner*—Anthony V. Ciarlante
*Attorney, Agent, or Firm*—Thomas R. Weaver; John H. Tregoning; C. Clark Dougherty, Jr.

[57] ABSTRACT

A method of determining the relative fracturability of two materials whereby samples of the materials are bonded together to form a composite sample and a force is applied to the composite sample to create and extend fractures therein. The rate of application of the force to the sample is controlled whereby the displacement of the sample resulting from the force increases at a relatively slow rate.

10 Claims, 7 Drawing Figures

METHOD OF DETERMINING THE RELATIVE FRACTURABILITY OF MATERIALS

The present invention relates generally to the determination of the fracturability of materials, and more particularly, but not by way of limitation, to an accurate method of determining the relative fracturability of two materials such as those which form subterranean rock formations.

In the production of fluids such as oil, gas and water from a subterranean rock formation penetrated by a well bore, a common technique employed for stimulating the production of desired fluids from the formation involves the creation and extension of fractures therein by applying a hydraulic force thereto. That is, a liquid fracturing fluid is pumped through the well bore penetrating the formation and into the formation at a rate such that the resultant hydraulic force exerted on the formation causes fractures to be created and extended therein. Commonly, the fractures are propped open after they are formed so that fluids contained in the formation readily flow through the fractures into the well bore.

Generally, subterranean rock formations are bounded by formations formed of dissimilar rock materials. Because of this, in carrying out fracture stimulation procedures in a formation from which it is desired to produce fluids, it is often necessary and always desirable to know the relative fracturabilities of the adjacent formations as compared to the formation to be fractured. For example, when the formation containing desired fluids is bounded by one or more formations containing undesired fluids, if it is known that the formations containing undesired fluids are more fracturable than the formation containing desired fluids, a fluid production stimulation procedure other than creating fractures is used because in fracturing the desirable formation, fractures will also be created in the undesirable formations. Conversely, however, if the formation containing desired fluids is more fracturable than adjacent formations, fractures can be created and extended in the desirable formation without extending into the undesirable formations.

Heretofore, a variety of methods of calculating the hydraulic force required for creating and extending fractures in subterranean rock formation, i.e., the fracturability of the formations, have been developed and used. However, due to the many factors which affect the fracturability of subterranean rock formations, assumptions must be made which often materially affect the accuracy of such calculations and make the results unreliable.

By the present invention, a method of determining the relative fracturability of materials is provided which is simple and accurate, and which is particularly suitable for determining the relative fracturability of subterranean rock formations.

In accordance with the present invention, samples of the materials between which the relative fracturability is to be determined are formed into comlementary shapes and bonded together along adjacent surfaces so that a composite sample is produced. A force is then applied to the composite sample so that the materials forming the sample are placed in tension in directions substantially parallel to at least a portion of the bonded surfaces thereof, and fractures are created and extended in the materials in directions transverse to the bonded surfaces. The displacement of the sample as a result of the force applied thereto is sensed while the fractures are created and extended, and the rate of application of the force to the sample is controlled in proportion to the sensed displacement so that the displacement increases at a selected relatively slow rate while the fractures are created and extended. The variations in the force applied to the sample while the materials forming it are fractured are observed so that the relative fracturability of the materials is determined.

In the drawings forming a part of this disclosure,

In the drilling of well bores penetrating subterranean formations, core samples of the formations are commonly obtained so that the materials from which the formations are made up can be observed, etc. Such core samples can be utilized in accordance with the present invention to determine the relative fracturability of the formations. That is, core samples of the rock formations between which it is desired to determine relative fracturability are formed into complementary shapes from which a composite sample is produced. While any of a variety of shapes can be utilized, one presently preferred shape of composite sample for testing in accordance with the present invention is cylindrical.

Figure 1:
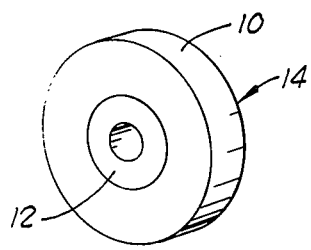
FIG. 1 is a perspective view of two materials between which the relative fracturability is to be determined formed into a preferred shape of composite sample.

Referring to FIG. 1, one of the materials to be tested is formed into a cylinder 10. The other material is then formed into a cylinder 12, the outside diameter of which is substantially equal to the inside diameter of the cylinder 10 so that the cylinders 10 and 12 can be fitted together as illustrated in FIG. 1 to form a composite cylindrical shape generally designated by the numeral 14. The adjacent annular surfaces of the cylinders 10 and 12 are cemented together with a high tensile strength cement or bonding material.

In preparing a composite sample from formation core samples which are generally cylindrical in shape, the outer diameter of the composite sample 14 is dictated by the available core sizes. An example of one procedure which can be used for preparing the composite sample 14 from core samples is to first prepare the outer cylinder 10 from one of the samples. The other sample is then machined on its outer surface into the cylinder 12 so that the outer surface of the cylinder 12 fits closely within the inner surface of the cylinder 10. The cylinders 10 and 12 are then bonded together, and after the bonding material has set, the composite sample 14 is machined on its flat faces so that it has a uniform thickness. A particularly suitable size of composite sample 14 for carrying out the method of the present invention is about 1 inch in depth, has an outside diameter of about 5 inches and an inside diameter of about 1 inch, with each of the cylinders 10 and 12 having wall thicknesses of about 1 inch.

Any of a variety of cementing or bonding materials can be utilized for bonding the samples 10 and 12 together so long as the bonding materials after setting has a strength equal to or greater than the strength of the materials from which the composite sample 14 is made up. Particularly suitable bonding agents for bonding rock maerials are commercially available epoxy resins which set quickly and have high tensile strengths.

Figure 2:
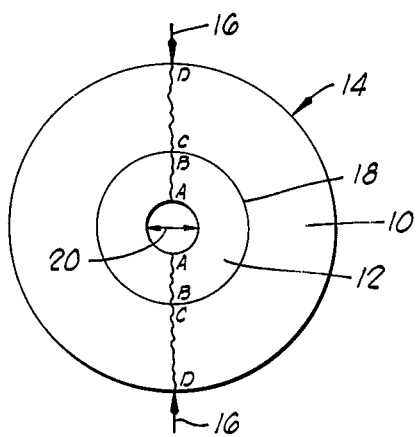
FIG. 2 is a side elevational view of the composite sample of FIG. 1 having fractures created and extended therein as a result of the application of force thereto.

In carrying out the method of the present invention for determining the relative fracturability of the materials 10 and 12 making up the composite sample 14, a compressive force can be applied to the outside annular surface of the composite sample 14 as illustrated by the arrows 16 in FIG. 2. Referring specifically to FIG. 2, when the force represented by the arrows 16 is applied to the composite sample 14 in a manner whereby the directions of the force approximately intersect the axis of the sample 14, the sample 14 is placed in compression in directions coincident with the directions of the compressive forces 16 and in tension in directions transverse to the directions of the compressive forces 16. As the compressive forces 16 are increased on the cylindrical sample 14, the tensile forces produced in directions transverse to the directions of the compressive forces increase, and as a result, the distance between the internal surfaces of the cylinder 14 in directions transverse to the directions of the compressive forces represented by the arrow 20 increases. That is, as the compressive forces 16 applied to the cylinder 14 are increased, the cylinder 14 is displaced in directions transverse to the directions of the compressive forces 16 and the tensile forces produced in the cylinder 14 in directions transverse to the directions of the compressive forces 16 increase.

In accordance with the present invention, the rate of application of the compressive forces 16 to the cylindrical sample 14 is controlled in a manner such that the displacement of the cylinder 14 resulting from the force applied thereto increases at a selected rate as fractures are created and extended therein. While a variety of methods and techniques can be utilized for sensing or measuring the displacement of the sample 14 resulting from the application of force thereto, and the displacement can be sensed or measured in any desired direction, a particularly suitable technique is to sense or measure increases in the distance between the internal surfaces of the cylinder 14 in the general direction represented by the arrow 20, i.e., in a direction transverse to the directions of the compressive forces 16. The rate of application of the compressive forces 16 to the sample 14 is controlled so that such distance increases at a selected relatively slow rate. As the displacement of the sample 14 increases, the tensile forces produced therein increase causing the sample to fracture and the fractures created to extend in directions coincident with the directions of the compressive forces 16.

A variety of apparatus can be utilized for applying the compressive forces 16 to the composite sample 14 and controlling the rate of application of such forces so that the displacement of the cylinder 14 increases at a selected rate. A particularly suitable apparatus and technique for accomplishing the foregoing is to sense the distance between the internal surfaces of the cylinder 14 in a direction corresponding to the arrow 20 by means of one or more conventional strain gauges installed within the interior of the cylinder 14. As the displacement of the cylinder 14 increases, a signal in direction proportion thereto is generated by the strain gauges. This signal is utilized to control the rate of application of compressive forces 16 on the sample 14, such as by means of a hydraulic press or loading machine and conventional control instruments, so that the displacement increases at a slow constant or other rate, and the rate of application of the forces 16 varies accordingly. That is, if the distance between the internal surfaces of the cylinder 14 increases too rapidly, the compressive forces applied by the hydraulic loading machine are reduced, and if the distance does not increase at a high enough rate, the compressive forces are increased accordingly.

By controlling the application of the compressive forces 16 applied to the sample 14 in the manner described above, the creation and propagation of fractures in the sample 14 is slowed down to the point whereby variations in the applied forces 16 and the relative fracturability of the materials making up the cylinder 14 can be observed and/or recorded.

Figure 3:
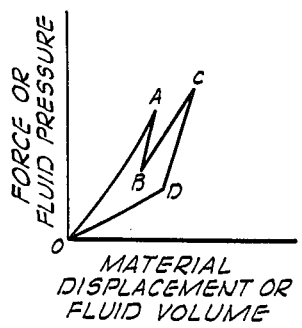
FIG. 3 is a graph illustrating the variations in the force applied to the composite sample of FIG. 2 versus displacement of the sample during the fracturing thereof.
Figure 4:
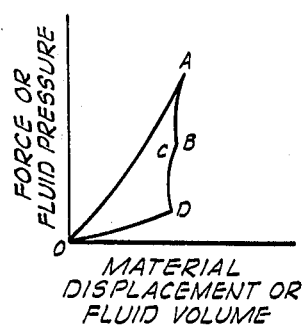
FIG. 4 is a graph similar to FIG. 3, but illustrating the variations in force applied to the composite sample versus displacement for a different arrangement of materials in the sample.
Figure 5:
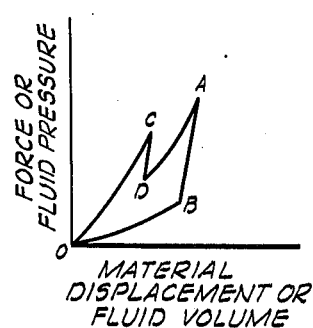
FIG. 5 is a graph similar to FIG. 4 illustrating different variations in applied force versus displacement during fracturing of the composite sample.

Referring now to FIGS. 3–5, graphs are presented illustrating the variations in the compressive forces 16 applied to the composite sample 14 while maintaining the displacement of the sample 14 in directions transverse to the directions of the compressive forces 16 at a controlled rate of increase for different arrangements of the materials 10 and 12 in the composite sample 14.

Referring specifically to FIGS. 2 and 3, let it be assumed that the material 12 making up the interior portion of the composite sample 14 is more fracturable than the material 10 making up the exterior portion of the sample. The compressive forces 16 are applied to the composite sample 14 in the manner described above, i.e., the rate of application of the compressive forces 16 is controlled so that the displacement of the sample is increased at a constant relatively slow rate, e.g., 0.00001 inch/second. FIG. 3 shows variations in the forces 16 applied to the composite sample 14 during the creation and extension of fractures therein versus the displacement of the sample in directions coincident to the directions of the compressive forces 16. That is, the compressive forces 16 increase to point A shown on FIG. 3 at which fractures are initiated in the material 12 on opposite sides of the interior of the cylindrical sample 14, i.e., at points A on FIG. 2. As the fractures created in the material 12 extend outwardly to the bonded surfaces 18 of the materials 10 and 12, i.e., the points B shown on FIG. 2, the compressive forces exerted on the sample 14 reduce to point B shown on FIG. 3. That is, in order to maintain the increase in displacement of the sample 14 at a constant rate during the extension of the fractures A–B in the material 12, the compressive forces applied to the sample 14 are reduced to point B on FIG. 3. Since the material 10 forming the outer portion of the sample 14 is less fracturable than the material 12, the force at point B on FIG. 3 is insufficient to extend the fractures into the material 10. Consequently, the force increases to point C shown on FIG. 3 during which time the factures A–B are stopped at the bonded surfaces 18 between the materials 10 and 12. When the forces applied reach the level required to initiate fractures in the material 10, i.e., point C shown on FIG. 3, fractures are initiated at points C shown on FIG. 2 in the material 10. As the fractures initiated at points C in the material 10 extend outwardly to the outer annular surfaces of the material 10, i.e., points D shown on FIG. 2, the forces applied to the sample 14 are reduced to point D shown on FIG. 3. An analysis of the variations in force recorded on FIG. 3 while the fractures A–B and C–D are created and extended in the composite sample 14 clearly shows that the material 12 forming the inner portion of the sample 14 is more fracturable than the material 10 forming the outer portion of the sample 14. That is, the force at point B required to extend fractures in the material 12 is less than the force at point C required to initiate fractures into the material 10, clearly indicating the material 12 to be more fracturable than the material 10.

Let it now be assumed that the material 12 forming the inner portion of the cylindrical sample 14 is less fracturable than the material 10 forming the outer portion thereof. Referring to FIGS. 2 and 4, when the compressive forces applied to the sample 14 increase to the point A shown on FIG. 4, fractures are initiated in the material 12 at points A shown on FIG. 2, followed by the extension of the fractures to points B at the bonded surfaces 18 between the materials 12 and 10. During the extension of the fractures from A to B in the material 12, the forces applied to the cylinder 14 reduce to the point B shown on FIG. 4. Since the material 12 is less fracturable than the material 10, less force is required to create and extend fractures in the material 10, and fractures are initiated at points C shown on FIG. 2 and at point C shown on FIG. 4 (coincident with point B). As the fractures in the material 10 extend from points C to points D, the forces exerted on the sample 14 reduce to point D shown on FIG. 4. Thus, an examination of FIG. 4 clearly shows that a greater force was not required to create fractures in the material 10 (point C) than the force required to extend fractures in the material 12, and that the material 12 is less fracturable than the material 10.

In certain instances where the material 12 forming the inner portion of the composite cylinder 14 is less fracturable than the material 10 forming the outer portion thereof, fractures are initiated and extended in the outer more fracturable material 10 prior to fractures being initiated and extended in the less fracturable material 12. This fracture mode results in a force versus displacement curve like that shown in FIG. 5. That is, the force exerted on the sample 14 increases to the level shown at point C on FIG. 5 whereby fractures are initiated at points C in the material 10 shown on FIG. 2. As the fractures extend to the points D shown on FIG. 2, the force is reduced to the level shown at point D on FIG. 5. Since the material 12 is less fracturable than the material 10, the force builds up to a higher level than that required to fracture the material 10, i.e., the level indicated at point A on FIG. 5 whereupon fractures are initiated in the material 12 at points A shown on FIG. 2. While the fractures extend from points A to points B in the material 12, the force is reduced to the level shown at point B on FIG. 5.

While the force versus displacement curves of FIGS. 3 and 5 are similar, they are distinguished during the carrying out of the method of the present invention by visual observation of which material 10 or 12 is fractured first. Thus, FIG. 5, with the visually observed fact that fractures were produced in the material 10 prior to the material 12 noted thereon, clearly shows that the material 12 is less fracturable than the material 10.

In another aspect of the present invention, instead of utilizing an external compressive force applied to the composite sample 14 for producing fractures therein and determining the relative fracturability of the materials making up the composite sample, force created by fluid under pressure injected within the interior of the composite cylindrical sample 14 is utilized. This technique best simulates hydraulic fracturing procedures used in fracturing subterranean formations penetrated by a well bore. In this aspect of the present invention, the composite cylindrical sample 14 is preferably first subjected to a constant external compressive force in the directions illustrated by the arrows 16 on FIg. 2 so that the sample will initially be placed in compression in such directions and fractures created in the sample 14 will follow such directions, i.e., directions coincident with the compressive forces produced therein. The compressive forces applied to the external surfaces of the composite cylinder 14 are of insufficient magnitude to cause fracturing of the sample 14. After the external compressive forces are applied to the sample 14, fluid under pressure is introduced into the interior of the cylinder 14, the rate of introduction and pressure of which is controlled in proportion to the displacement of the sample in the same manner as decribed above. That is, increases in the distance between opposite surfaces of the interior of the cylinder 14 are measured while fluid under pressure is injected into the interior of the cylinder 14, and the rate of injection and pressure of the fluid is controlled in proportion to increases in such distances so that such distance increases at a controlled rate while fractures are created and extended in the cylinder 14. Increasing fluid pressure within the interior of the sample displaces the sample in every direction including directions transverse to the directions of the compressive forces.

The results produced when fluid under pressure is introduced into the interior of the cylinder 14 are substantially indentical to the results produced when an external force only is utilized, except that fractures in the composite sample will always be initiated at points A and never at points C shown on FIG. 2. Thus, when the fluid pressure applied to the sample 14 is plotted versus injected fluid volume, curves result which are similar to the curves illustrated in FIGS. 3–5. That is, when the material 12 forming the inner portion of the composite cylinder 14 is more fracturable than the material 10 forming the outer portion thereof, a curve similar to FIG. 3 results. When the material 12 forming the inner portion of the cylinder 14 is less fracturable than the material 10 forming the outer portion thereof, the fluid pressure versus injection fluid volume curve generated is similar to the curve illustrated in FIG. 4.

As will be understood by those skilled in the art, the particular configuration or shape of the composite test sample depends largely on the shape of the material samples which are available. As mentioned above, core samples obtained in the drilling of well bores penetrating subterranean formations are generally cylindrical in shape and readily lend themselves to the formation of a composite sample of cylindrical shape as illustrated in FIG. 1. In other cases, it may be desirable or necessary to form the samples into rectangular hexahedral shapes as illustrated in FIG. 6, or into other similar shapes.

Figure 6:
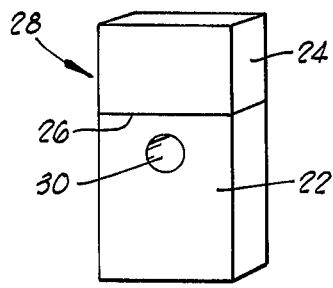
FIG. 6 is a perspective view of two materials formed into a composite sample of alternate shape.

Referring specifically to FIG. 6, in this event the materials 22 and 24 are formed into rectangular hexahedral or other similar shapes and are bonded together along adjacent surfaces 26 to form a composite sample generally designated by the numeral 28. An aperture 30, preferably circular in cross-section, is formed in the material 22. Preferably, the material 22 containing the aperture 30 is of a height greater than the height of the material 24 so that the center of the aperture 30 is substantially equidistant from the top and bottom of the composite sample 38 with the aperture 30 lying entirely within the material 22.

Figure 7:
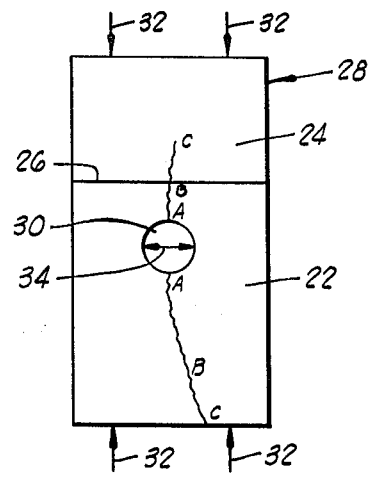
FIG. 7 is a side elevational view of the composite sample of FIG. 6 having fractures created and extended therein as a result of the application of force thereto.

Referring now to FIG. 7, in determining the relative fracturability of the materials 22 and 24 of the composite sample 28, a constant external force is applied to the sample 28 in directions illustrated by the arrows 32. This force applied to the sample 28 produces tensile forces therein adjacent the aperture 30 in directions transverse to the directions of the compressive forces as shown by the arrow 34. Since the tensile forces produced lie substantially parallel to the bonded surfaces 26 of the materials 22 and 24, fractures produced in the composite sample 28 by the introduction of fluid under pressure into the aperture 30 will run in directions coincident with the directions of the compressive force and transverse to the bonded surfaces 26. In order to determine the relative fracturability of the materials 22 and 24 in accordance with the present invention, the fractures produced in the materials 22 and 24 must intersect the bonded surfaces 26 thereof.

After applying the constant compressive force described above of a magnitude sufficient to place the composite sample 28 in compression and tension, but not of a magnitude sufficient to fracture the materials 22 and 24 thereof, fluid under pressure is introduced into the aperture 30. The rate of introduction and pressure of the fluid is controlled in proportion to the displacement of the sample 28 so that the displacement increases at a controlled rate. The displacement of the composite sample 28 resulting from the injection of fluid under pressure into the aperture 30 is measured or sensed in the same manner as described above for the composite sample 14, i.e., the distance between internal surfaces of the aperture 30 in directions shown by the arror 34 preferably transverse to the directions of fractures produced therein is continuously measured by means of one or more conventional strain gauges so that a control signal proportional to changes in such distance is produced. This control signal is fed to conventional instruments and controls which in turn operate a fluid pump or other means for producing the fluid under pressure injected into the interior of the aperture 30. That is, the injection of the fluid and the pressure thereof are controlled in a manner whereby the displacement of the sample 28 resulting from the exertion of fluid pressure within the aperture 30 increases at a selected rate as fractures are created and extended in the materials 22 and 24 thereof.

Referring to FIG. 7, as the fluid pressure applied to the sample 28 increases, fractures are created in the material 22 at points A and are extended to points B. If the upper fracture A–B stops at the bonded surfaces 26 of the materials 22 and 24 while the lower fracture A–B extends to point C, then it is clear that the material 22 is more fracturable than the material 24. If the upper fracture A–B propagates into the material 24 and extends to point C therein, then the length of the upper fracture in the materials 22 and 24, i.e., the length A–C is compared with the length A–C of the lower fracture in the material 22. If the length A–C of the upper fracture in the materials 22 and 24 is less than the length A–C of the lower fracture in the material 22, then it is clear that the material 22 is more fracturable than the material 24. Conversely, if the length of the upper fracture A–C is greater than the length of the lower fracture A–C, it is clear that the material 22 is less fracturable than the material 24. If the length of the fractures A–C are the same, then the fracturabilities of the materials 22 and 24 are substantially equal.

Thus, by the method of the present invention, the relative fracturability of two unknown materials can be quickly and simply determined by forming a composite sample of the materials wherein the two materials are bonded together along adjacent surfaces and then applying a force to the bonded samples whereby fractures are created and extended therein in directions transverse to the bonded surfaces. The displacement of the composite sample, most suitably in directions transverse to the directions of fractures formed therein, is sensed and the rate of application of the force, applied either externally or internally, is controlled in proportion to the sensed displacement whereby the displacement increases at a selected slow rate while the fractures are created and extended in the sample. This control of the creation and extension of fractures in the sample slows down the fracturing process and permits visual observation of the fractures as they are formed as well as the observation and recording of the variations in force or pressure so that the relatively fracturability of the materials is determined.

As stated above, any of a variety of force or load producing apparatus in conjunction with strain gauge and/or other control apparatus can be utilized, and the force applied to the composite sample can be created by externally loading the sample or internally loading the sample by introducing fluid under pressure within an aperture or opening formed therein. In the latter case, the composite sample must be confined in a manner whereby the fluid under pressure does not escape through the faces of the sample as fractures are created therein. As presently preferred technique for confining the fluid under pressure to the sample being fractured is to bond clear plastic material to the faces of the sample so that the fluid under pressure is confined and the hydraulic fracturing of the materials can be visually observed. While a variety of clear plastic and bonding materials can be utilized, a presently preferred clear plastic material for such use is plexiglass bonded to the faces of the sample by means of a quick-setting, high-strength bonding agent. A technique which can be employed to achieve an even bond between the faces of the sample and the plexiglass is to first dry the sample to remove all moisture therefrom. The faces of the sample are then coated with an agent which makes the faces wettable by the bonding agent used, e.g., an organo-functional silane, followed by a coating of the bonding agent. The plexiglass is next pressed onto the bonding agent and the bonding agent is allowed to set. In order to insure that an even layer of bonding agent remains between the sample faces and plexiglass and to insure that the bonding agent sets evenly, a plurality of holes or apertures are drilled through the plexiglass so that when the plexiglass is pressed onto the bonding agent-coated faces of the sample, the bonding agent is squeezed through the holes and a constant layer of bonding agent is left between the sample faces and the plexiglass surfaces. The even setting of the bonding agent is facilitated by the exposure to the atmosphere by way of the holes in the plexiglass. A particularly suitable bonding agent for bonding plexiglass to rock samples is a commercially available silicone adhesive.

EXAMPLE

A hydraulic fracturing procedure is carried out in a sandstone formation penetrated by a well bore to increase the productivity of oil and gas therefrom. Based on less than desirable production of oil and gas from the sandstone formation after the fracturing procedure is completed, the question arises concerning whether the fracture or fractures initiated in the sandstone formation could have propagated into the adjacent shale formation thereby accounting for the less than desirable results.

Core samples of the shale and sandstone formations are formed into cylindrical shapes and a composite sample of the type illustrated in FIG. 1 is prepared having the inside cylindrical portion 12 formed from the shale and the outside cylindrical portion 10 formed from the sandstone. An external compressive force is applied to the composite sample and the sample is fractured in accordance with the method of the present invention described above whereby the rate of application of the external compressive force is controlled in proportion to the displacement of the sample so that the displacement increases at a controlled rate while the sample is fractured. The variations in the force applied to the sample while the fractures are created and extended are recorded and a force versus displacement curve similar to FIG. 5 is produced. For an examination of the curve, it is readily apparent that the shale inner portion of the sample 14 is more fracturable than the sandstone outer portion thereof, and consequently, the fractures initiated in the sandstone formation could have propagated into the shale formation. From

What is claimed is:

1. A method of determining the relative fracturability of two materials comprising the steps of:
   a. forming samples of said materials into complementary shapes;
   b. bonding said materials together along adjacent surfaces to form a composite sample thereof;
   c. applying a force to said composite sample whereby fractures are created and extended in said materials in directions transverse to said bonded surfaces;
   d. sensing the displacement of said sample resulting from the application of said force thereto while said fractures are created and extended in said sample;
   e. controlling the rate of application of said force to said sample in proportion to said sensed displacement whereby said displacement increases at a selected rate while said fractures are created and extended in said sample; and
   f. observing the variations in said force applied to said sample while said sample is fractured so that the force required to create and extend fractures in said materials and the relative fracturability of said materials and determined.

2. The method of claim 1 wherein said materials are formed into cylindrical shapes with the outside diameter of one material being substantially equal to the inside diameter of the other material and wherein said materials are fitted together and bonded around the annular adjacent surfaces thereof whereby a single composite cylindrical sample is formed therefrom.

3. The method of claim 2 wherein said force applied in accordance with step (c) is applied as a compressive force to the external annular surface of said composite cylindrical sample in a direction intersecting the axis of said sample whereby said sample is placed in tension in directions transverse to the directions of said compressive force and is fractured in directions coincident with the directions of said compressive force.

4. The method of claim 3 wherein step (d) comprises sensing increases in the distance between opposite internal surfaces of said composite cylindrical sample along a line transverse to the directions of said fractures formed therein.

5. The method of claim 4 which is further characterized to include the step of recording said variations in force applied to said sample versus the displacement of said sample in directions transverse to the directions of said fractures.

6. The method of claim 2 wherein said force applied in accordance with step (c) is applied by introducing fluid under pressure into the interior of said composite cylindrical sample, the rate of introduction and pressure of said fluid being controlled in accordance with step (e).

7. The method of claim 6 wherein step (d) comprises sensing increases in the distance between opposite terminal surfaces of said composite cylindrical sample along a line transverse to the directions of said fractures formed therein.

8. The method of claim 7 which is further characterized to include the step of recording variations in the pressure of said fluid introduced into the interior of said cylindrical sample versus the volume of fluid introduced into the interior of said sample.

9. A method of determining the relative fracturability of two materials comprising the steps of:
   a. forming samples of said materials into complementary shapes;
   b. bonding said materials together along adjacent surfaces thereof to form a composite sample therefrom;
   c. forming an aperture in said composite sample through one of said materials;
   d. applying a compressive force to said composite sample in a direction transverse to the bonded surfaces of said materials whereby said material containing said aperture is placed in tension adjacent said aperture in directions transverse to the directions of said compressive force but said material is not fractured by the resultant tensile force;
   e. introducing fluid under pressure into the interior of said aperture while maintaining said compressive force on said composite sample whereby said fluid under pressure causes fractures to be created and extended in said materials in directions transverse to the bonded surfaces thereof;
   f. sensing the displacement of said material containing said aperture resulting form the introduction of fluid under pressure thereinto;
   g. controlling the rate of introduction and the pressure of said fluid in the interior of said aperture in proportion to said sensed displacement of said material containing said aperture whereby said displacement increases at a selected rate while said fractures are created and extended in said materials; and
   h. observing the length of fractures formed in said materials to thereby determine the relative fracturability of said materials.

10. The method of claim 9 wherein said materials and said composite sample are formed in rectangular hexahedral shapes.

* * * * *